(12) United States Patent
Li et al.

(10) Patent No.: US 8,642,887 B1
(45) Date of Patent: Feb. 4, 2014

(54) METALLIZATION BARRIER FOR A HERMETIC FEEDTHROUGH

(75) Inventors: Dongfa Li, East Amherst, NY (US); Ashish Shah, East Amherst, NY (US)

(73) Assignee: Greatbatch Ltd., Clarence, NY (US)

( * ) Notice: Subject to any disclaimer, the term of this patent is extended or adjusted under 35 U.S.C. 154(b) by 55 days.

(21) Appl. No.: 13/310,866

(22) Filed: Dec. 5, 2011

Related U.S. Application Data

(60) Provisional application No. 61/419,374, filed on Dec. 3, 2010.

(51) Int. Cl.
*H01J 5/00* (2006.01)

(52) U.S. Cl.
USPC ............. 174/50.6; 174/650; 607/37; 361/302

(58) Field of Classification Search
USPC ........... 174/650, 50.6, 35 R; 361/302; 607/37
See application file for complete search history.

(56) References Cited

U.S. PATENT DOCUMENTS

| | | | | |
|---|---|---|---|---|
| 6,852,925 | B2* | 2/2005 | Wolf et al. | 174/50.6 |
| 7,145,076 | B2* | 12/2006 | Knappen et al. | 174/50.6 |
| 7,564,674 | B2* | 7/2009 | Frysz et al. | 361/302 |

OTHER PUBLICATIONS

Ajay K. Misra, Reaction of Ti and Ti—Al Alloys with Alumina, Metallurgical Transactions, vol. 22A, Mar. 1991, pp. 715-721, US.
Rocha et al, Electrochemical Behavior of Ti/Al2O3 Interfaces Produced by Diffusion Bonding, vol. 6, No. 4, pp. 439-444, 2003, US.
Kang et al., Interactions between Ti and alumina-based ceramics, Journal of Materials Science 27 (1992) pp. 4536-4544, US.

\* cited by examiner

*Primary Examiner* — Dhirubhai R Patel
(74) *Attorney, Agent, or Firm* — Michael F. Scalise

(57) ABSTRACT

A metallization that includes a composite of alternating metal and metal oxide layers for incorporation into feedthrough filter capacitor assemblies is described. The feedthrough filter capacitor assemblies are particularly useful for incorporation into implantable medical devices such as cardiac pacemakers, cardioverter defibrillators, and the like, to decouple and shield internal electronic components of the medical device from undesirable electromagnetic interference (EMI) signals.

16 Claims, 6 Drawing Sheets

METALLIZATION BARRIER FOR A HERMETIC FEEDTHROUGH

CROSS REFERENCE TO RELATED APPLICATIONS

This application claims priority to U.S. provisional application Ser. No. 61/419,374, filed on Dec. 3, 2010.

BACKGROUND OF THE INVENTION

1. Field of the Invention

This invention relates generally to a hermetic feedthrough terminal pin assembly, preferably of the type incorporating a filter capacitor. More specifically, this invention relates to metallization comprising oxidized titanium for incorporation into feedthrough filter capacitor assemblies, particularly of the type used in implantable medical devices such as cardiac pacemakers, cardioverter defibrillators, and the like, to decouple and shield internal electronic components of the medical device from undesirable electromagnetic interference (EMI) signals. The metallization provides a surface with which a hermetic seal can be established that prevents passage or leakage of fluids through the feedthrough assembly and into the medical device.

2. Prior Art

Feedthrough assemblies are generally well known in the art for use in connecting electrical signals through the housing or case of an electronic instrument. For example, in an implantable medical device, such as a cardiac pacemaker, defibrillator, or neurostimulator, the feedthrough assembly comprises one or more conductive terminal pins supported by an insulator structure for passage of electrical signals from the exterior to the interior of the medical device. The conductive terminals are fixed into place using a metallization and gold braze process, which provides a hermetic seal between the pin and insulative material.

Conventionally, a metallization is composed of a combination of discrete layers of untreated titanium metal and molybdenum or titanium metal and niobium have been used to facilitate bonding of the gold to the insulative material. Untreated titanium metal is widely used as an adhesion layer to provide bonding between a ceramic material, particularly that of alumina, and a different metal. However, the untreated titanium metal typically reacts with gold to form an intermetallic alloy. Intermetallic alloy metals such as those formed by the combination of titanium and gold, typically result in an undesirable brittle bond which may result in loss of hermeticity. Titanium metal is known to have a high diffusion coefficient in liquid gold which increases its tendency to diffuse within gold and form these intermetallic alloy phases. Typically when such metals are brazed, the titanium metal departs or lifts from the surface of the insulator material and forms an intermetallic alloy with the gold braze material.

As a result, a barrier layer comprising molybdenum or niobium is applied to the outer surface of the titanium. This additional layer is designed to act as a barrier layer to prohibit the migration of titanium from the surface of the insulator material and thus prevent the formation of a titanium and gold intermetallic. While materials such as molybdenum and niobium typically provide adequate metallization barrier layers, recent work has been focused on an improved metallization layer through incorporation of an oxidized layer of titanium as a means to facilitate bonding of ceramic with that of a metal with minimized migration of the metallization layer. The diffusion rate for the oxidized titanium in gold is less than that of the untreated titanium. Therefore, the metallization comprising the oxidized metal is less likely to lift from the surface of the insulator and form an intermetallic phase with the gold braze material.

SUMMARY OF THE INVENTION

In a preferred form, a feedthrough filter capacitor assembly according to the present invention comprises an outer ferrule hermetically sealed to either an alumina insulator or fused glass dielectric material seated within the ferrule. The insulative material is also hermetically sealed to at least one terminal pin. That way, the feedthrough assembly prevents leakage of fluid, such as body fluid in a human implant application, past the hermetic seal at the insulator/ferrule and insulator/terminal pin interfaces.

According to the invention, the metallization used to facilitate the formation of the hermetic seal of a feedthrough assembly preferably comprises a composite of alternating layers of metal and metal oxide. Specifically, a layer of a first metal, particularly titanium, is deposited on the surface of an insulator material, such as alumina. The layer of the first metal is then subsequently subjected to a heat treatment process that transforms a portion of the metal layer into an oxidized metal layer establishing a metallization layer comprised of two distinct layers, one being that of a layer of metal, the other being a layer of oxidized metal. In an alternate embodiment, additional layers of alternating metal and metal oxide may be layered onto the second metal oxide layer.

The metal and oxidized layered metallization provides improved bonding to the surface of the insulator which is less susceptible to metallization migration. The metallization is also biocompatible and, therefore, provides a long term bonding interface that is immune to the body.

These and other objects and advantages of the present invention will become increasingly more apparent by a reading of the following description in conjunction with the appended drawings.

DETAILED DESCRIPTION OF THE PREFERRED EMBODIMENTS

Figure 1:
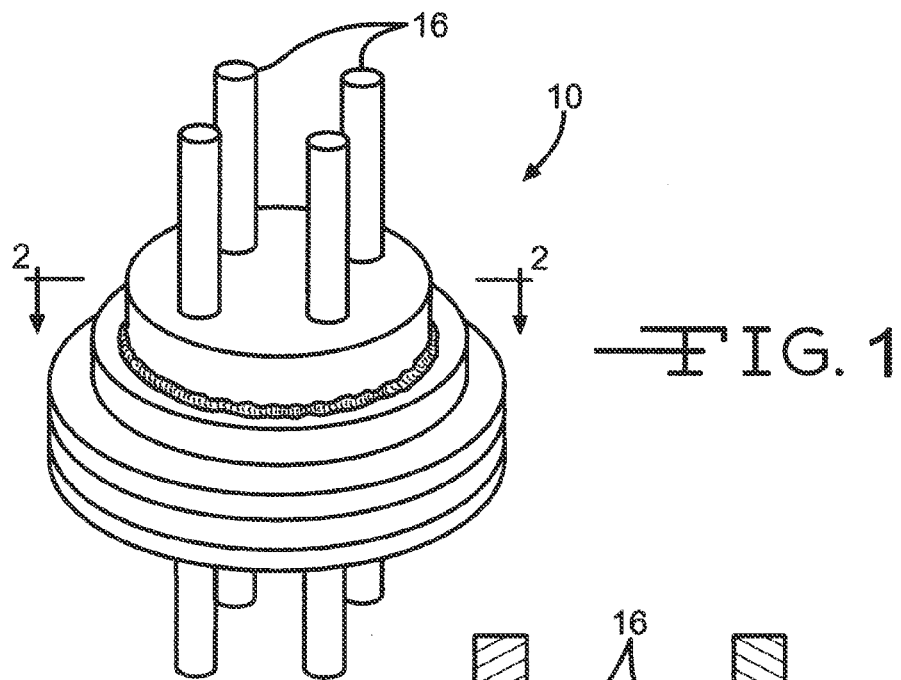
FIG. 1 illustrates a perspective view of an embodiment of a feedthrough assembly.
Figure 2:
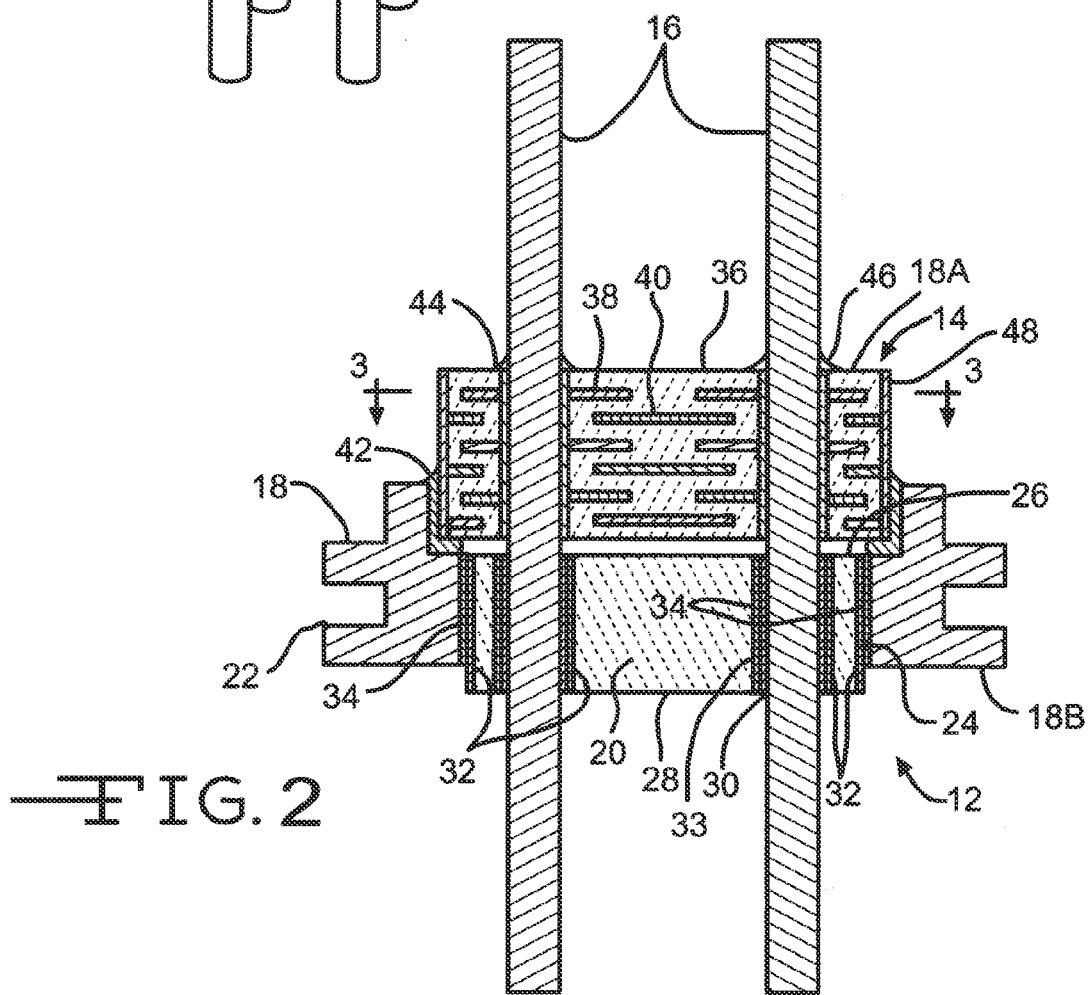
FIG. 2 shows a cross-sectional view of the feedthrough assembly taken along line 2-2 of FIG. 1.
Figure 3:
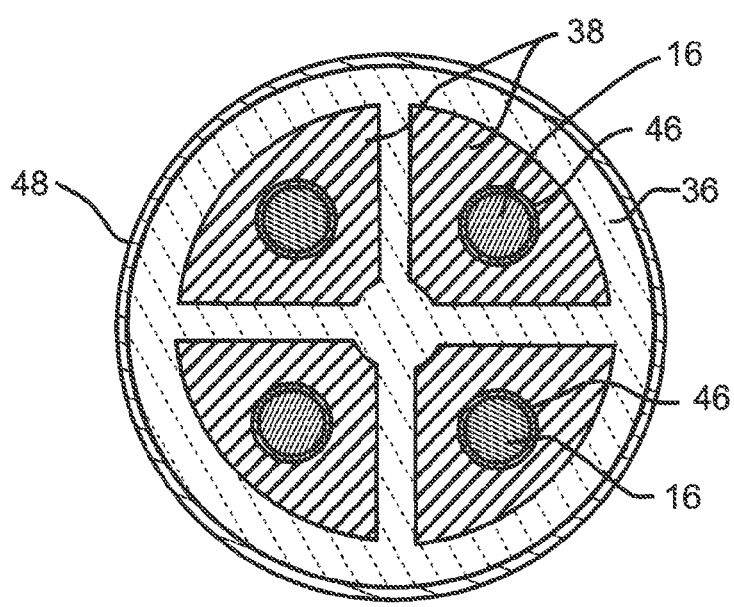
FIG. 3 illustrates a cross-sectional view of the feedthrough assembly taken along line 3-3 of FIG. 2.

Referring now to the drawings, FIGS. 1 through 3 illustrate an internally grounded feedthrough capacitor assembly 10 comprising a feedthrough 12 supporting a filter discoidal capacitor 14. The feedthrough filter assembly 10 is useful with medical devices, preferably implantable devices such as pacemakers, cardiac defibrillators, cardioverter defibrillators, cochlear implants, neurostimulators, internal drug pumps, deep brain stimulators, hearing assist devices, incontinence devices, obesity treatment devices, Parkinson's disease therapy devices, bone growth stimulators, and the like. The feedthrough 12 portion of the assembly 10 includes terminal pins 16 that provide for coupling, transmitting and receiving electrical signals to and from a patient's heart, while hermetically sealing the interior of the medical instrument against ingress of patient body fluids that could otherwise disrupt instrument operation or cause instrument malfunction. While not necessary for accomplishing these functions, it is desirable to attach the filter capacitor 14 to the feedthrough 12 for suppressing or decoupling undesirable EMI signals and noise transmission into the interior of the medical device.

More particularly, the feedthrough 12 of the feedthrough filter capacitor assembly 10 comprises a ferrule 18 defining an insulator-receiving bore formed by a ferrule sidewall extending from a first ferrule end 18A to a second ferrule end 18B, the ferrule sidewall surrounding an insulator 20. Suitable electrically conductive materials for the ferrule 18 include titanium, tantalum, niobium, stainless steel or combinations of alloys thereof, the former being preferred. The ferrule 18 may be of any geometry, non-limiting examples being round, rectangle, and oblong. A surrounding flange 22 extends from the ferrule 18 to facilitate attachment of the feedthrough 10 to the casing (not shown) of, for example, one of the previously described implantable medical devices. The method of attachment may be by laser welding or other suitable methods.

The insulator 20 is of a ceramic material such as of alumina, zirconia, zirconia toughened alumina, aluminum nitride, boron nitride, silicon carbide, glass or combinations thereof. Preferably, the insulating material is alumina, which is highly purified aluminum oxide, and comprises a sidewall 24 extending to a first upper side or end 26 and a second lower side or end 28, The insulator 20 is also provided with bores 30 that receive the terminal pins 16 passing therethrough. A layer of metal 32, referred to as metallization, is applied to the insulator sidewall 24 and to a bore sidewall 33 of the terminal pin bores 30 to aid a braze material 34 in hermetically sealing between the ferrule 18 and the outer sidewall 24 of the insulator 20 and between the terminal pins 16 and the bore sidewall 33 of the insulator 20, respectively. Specifically, the metallization layer 32 is preferably applied to a portion of the outer surface of the insulator sidewall 24 and to a portion of the surface of the inside sidewall 33 of the terminal pin bores 30. These surfaces are intended to contact and bond with the ferrule 18 and terminal pins 16, respectively, of the feedthrough assembly 10, establishing a hermetic seal therebetween.

Figure 4:
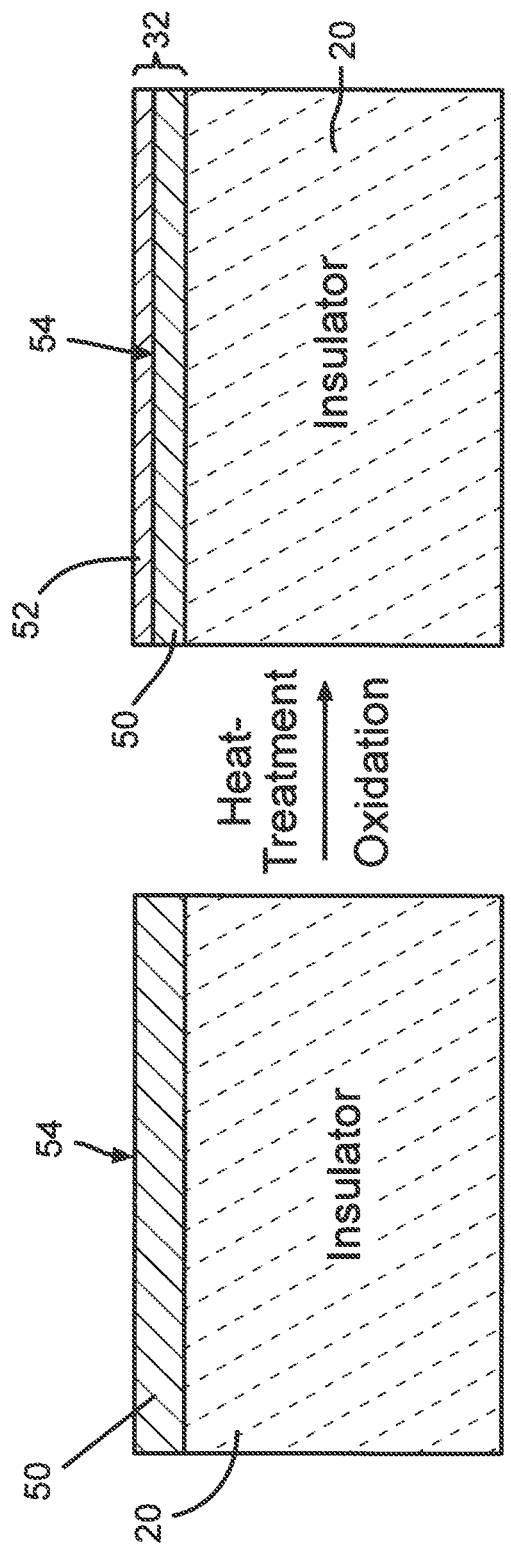
FIG. 4 illustrates an embodiment of the present invention of a metallization layer comprising a first metal layer and a second metal oxide layer.
Figure 5:
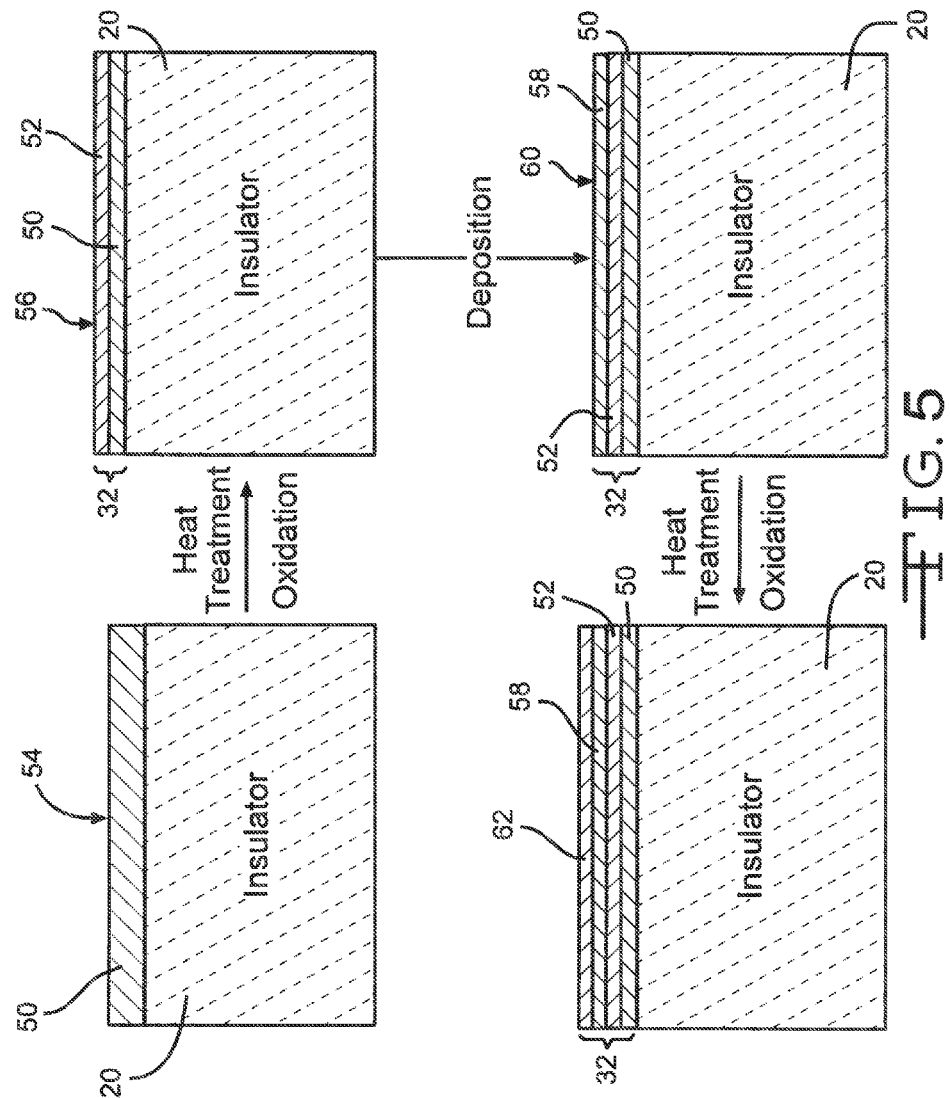
FIG. 5 shows an alternate embodiment of the present invention of a metallization layer comprising a first metal layer, a second metal oxide layer, a third metal layer and a fourth metal oxide layer.

According to one embodiment of the present invention, as shown in FIGS. 4 and 5, the metallization 32 comprises a composite of a first metal layer 50 and a second metal oxide layer 52. As illustrated, the second metal oxide layer 52 resides on a first metal top surface 54 of the first metal layer 50, the metal layer 50 being deposited on a surface of the insulator 20. More specifically, the second metal oxide layer 52 is bonded to the first metal top surface 54 of the first metal layer 50 which is bonded to a portion of a surface of the insulator sidewall 24 and/or a portion of a surface of the bore sidewall 33.

In a preferred embodiment, the first metal layer 50 is composed of titanium and titanium alloys. The second metal oxide layer 52 is preferably composed of oxidized titanium or oxidized titanium alloys thereof. Examples of titanium oxide may comprise $Ti_2O_3$ or $TiO_2$. Although the use of titanium and its associated alloys are preferred, it is contemplated that other metals such as molybdenum, niobium, tungsten, aluminum, vanadium and their associated alloys may also be used as the first metal layer 50. Furthermore, the associated oxides of these metals or their associated alloys may comprise the second metal oxide layer 52.

In a preferred embodiment, the metallization 32 has an overall thickness ranging from about 0.01 um to about 25 um. In a more preferred embodiment, the metallization 32 has a thickness ranging from about 0.50 um to about 5.0 um. Most preferably, the metallization 32 has a thickness ranging from 1.0 um to about 2.0 um. The thickness of the second metal oxide layer 52 comprises from about 25 percent to about 50 percent of the total metallization layer thickness. The thickness of the first metal layer 50 comprises from about 50 percent to about 75 percent of the total metallization layer thickness. Therefore, the second metal oxide layer 52 may comprise a thickness ranging from about 0.0025 um to about 12.5 um, more preferably from about 0.25 um to about 1.0 um.

In a preferred embodiment, the first metal layer 50 is initially applied to the surface of the insulator 20. The first metal layer 50 may be applied to the surface of the insulator 20 by various means including, but not limited to, sputtering, electron-beam deposition, pulsed laser deposition, plating, electroless plating, chemical vapor deposition, vacuum evaporation, thick film application methods, and aerosol spray deposition, and thin cladding. Once the first metal layer 50 is applied to the surface of the insulator 20, the metalized substrate is subsequently heat treated in an ambient atmosphere. Although the use of an ambient atmosphere is preferred, the metalized insulator may also be heat treated in an oxygen rich atmosphere. Such an oxygen rich atmosphere may be used to control the attributes of the second metal oxide layer 52 such as its thickness, density, molecular oxygen ratio, and/or morphology of the oxide layer. "Morphology" is herein defined as the texture of a surface, such as that of the second oxide layer 52. The oxide layer 52 may have a surface morphology that is smooth, rough or undulated. A "smooth" morphology is primarily characterized by a planar surface. A "rough" morphology is primarily characterized by a surface comprising jagged edges and an "undulated" morphology is primarily characterized by a surface comprising a series of elevated regions.

In a preferred embodiment, the titanium is heat treated at a temperature ranging from about 600° C. to about 1,000° C. for about 30 minutes to about 180 minutes. More preferably, the first metal layer 50 is heat treated at a temperature ranging from about 750° C. to about 850° C. for about 60 to about 120 minutes. This heat treating process preferably diffuses oxygen into the chemical structure of the first metal layer 50, thereby transforming a portion of the metal into a layer of oxidized metal, such as that of the second metal oxide layer 52, as shown in FIG. 4. It is noted that the heat treatment process may be performed within the metal deposition instrument or outside the metal deposition instrument, such as in a heat treating oven (not shown). For example, the first metal layer 50 may be applied using sputtering and subsequently heat treated within the sputtering chamber of the instrument, thereby eliminating the need to remove the metalized insulator 20. In a specific example, the surface of an alumina insulator 20 is metalized with about 1.5 um of titanium, forming the first metal layer 50. The metalized layer of titanium is then heat treated at about 800° C. for about 90 minutes to form the second metal oxide layer 52 of titanium oxide.

In a second embodiment, as illustrated in FIG. 5, a third metal layer 58 may be applied to the second metal oxide layer 52. More specifically, an additional layer of metal, such as titanium, may be applied to a surface 56 of the second metal oxide layer 52. Although titanium and its associated alloys are preferred, the third metal layer 58 may comprise other metals comprising molybdenum, niobium, tungsten, aluminum, vanadium and their associated alloys.

In a preferred embodiment, the third metal layer 58 having a thickness ranging from about 0.01 um to about 5.0 um, more preferably a thickness ranging from about 0.10 um to about 2.0 um is deposited on the surface 56 of the second metal oxide layer 52. The insulator 20, now comprising an additional third metal layer 58, is again heat treated in an ambient atmosphere at a temperature ranging from about 200° C. to about 500° C. for about 10 minutes to about 60 minutes. More preferably the insulator 20, comprising the first metal layer 50, the second metal oxide layer 52 and the third metal layer 58, is heat treated at a temperature ranging from about 300° C. to about 400° C. for about 30 minutes. Similarly to the first heat treatment, as previously discussed, an oxygen rich atmosphere may also be used.

The second heat treatment process preferably forms a fourth metal oxide layer 62 that resides on a surface 60 of the third metal layer 58. More specifically, the fourth metal oxide layer 62 is chemically bonded to the surface 60 of the third metal layer 58. Therefore, as shown in FIG. 5, the metallization 32 comprises a four layer composite comprising the first metal layer 50, the second metal oxide layer 52, the third metal layer 58 and the fourth metal oxide layer 62. It is contemplated that the metallization layer 32 could also be constructed with additional alternating layers of similar or dissimilar metals and metal oxides.

In a specific example of the second embodiment of the present invention, the surface of an alumina insulator 20 is metalized with a first metal layer 50 of titanium with a thickness of about 0.5 um. The first layer of titanium is then heat treated at about 800° C. for about 90 minutes to form the second metal oxide layer 52. After the first heat treatment, an additional layer of about 1.0 um of titanium, i.e., the third metal layer 58 is applied to the surface 56 of the second layer of titanium oxide. This third metal layer 58 of titanium is then heat treated a second time at about 350° C. for about 30 minutes.

Similar to the application of the first metal layer 50, the third metal layer 58 and subsequent metal layers may be applied using various means including, but not limited to, sputtering, electron-beam deposition, pulsed laser deposition, plating, electroless plating, chemical vapor deposition, vacuum evaporation, thick film application methods, and aerosol spray deposition, and thin cladding.

The composite construction comprising alternating layers of metal and metal oxide establish a metallization layer 32 with improved bonding characteristics, particularly compared to those comprising distinct layers of titanium and molybdenum as well as titanium and niobium. The composite metal and oxide layers are bonded together such that diffusion of the metal layer, particularly that of titanium, into the gold braze material is impeded. In other words, the present invention provides a layered metallization 32 that provides improved boding between the insulator 20 and the first metal layer 50 as well as the oxide metal layers 58, 62 comprising the top layer of the metallization 32, and the braze material.

Figure 6:
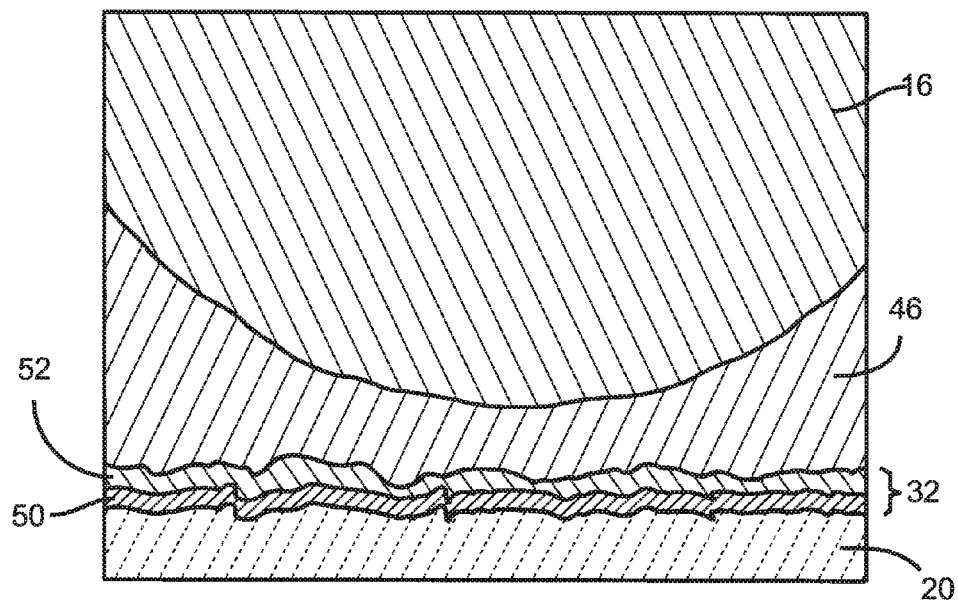
FIG. 6 is an illustration of a cross-sectional view of an embodiment of a brazed terminal pin.
Figure 7:
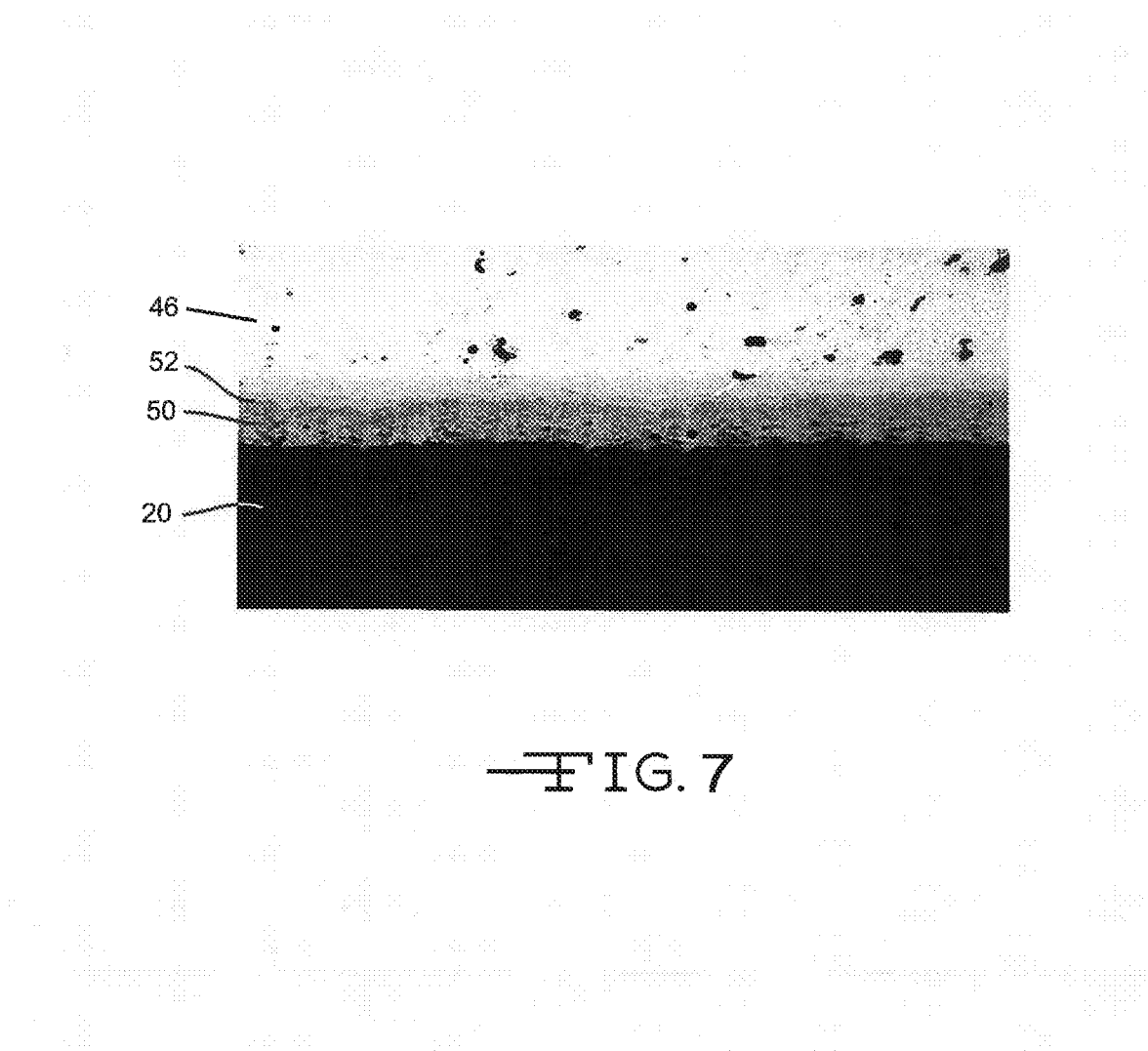
FIG. 7 is a photograph depicting a cross-sectional view of an embodiment of a brazed terminal pin.

As illustrated in FIGS. 6 and 7, the first metal layer 50, at the bottom side of the metallization, is shown forming a bond between the insulator material. In an embodiment, a bond comprising TiAl, Ti$_3$Al or combinations thereof is preferably formed between the first metal layer 50 and the surface of the insulator 20. Likewise at the opposite side or top layer of the metallization 32, a bond between the oxidized metal, particularly oxidized titanium and gold is formed.

Referring to FIGS. 1 through 3, non-limiting examples of terminal pins 16 include platinum, platinum alloys, particularly platinum-iridium alloys, palladium and palladium alloys. Furthermore, it is contemplated that the terminal pin 16 may comprise an exterior outer terminal pin coating or layer of platinum, platinum alloys, gold, silver, palladium and palladium alloys. The core terminal pin material may be selected from the group consisting of niobium, tantalum, nickel-titanium (NITINOL®), titanium, particularly beta titanium, titanium alloys, stainless steel, molybdenum, tungsten, platinum, and combinations thereof. The means of coating may include sputtering, cladding, and or plating. The coating may be applied through a process of sputtering, electron-beam deposition, pulsed laser deposition, plating, electroless plating, chemical vapor deposition, vacuum evaporation, thick film application methods, aerosol spray deposition, and thin cladding.

In addition, non-limiting examples of braze materials include gold, gold alloys, and silver. Then, if the feedthrough 10 is used where it will contact bodily fluids, the resulting brazes do not need to be covered with a biocompatible coating material. In other embodiments, if the brazes are not biocompatible, for example, if they contain copper, they are coated with a layer/coating of biocompatible/biostable material. Broadly, the biocompatibility requirement is met if contact of the braze/coating with body tissue and blood results in little or no immune response from the body, especially thrombogenicity (clotting) and encapsulation of the electrode with fibrotic tissue. The biostability requirement means that the braze/coating remains physically, electrically, and chemically constant and unchanged over the life of the patient.

As further shown in FIGS. 1 through 3, the feedthrough filter capacitor 10 includes the filter capacitor 14 that provides for filtering undesirable EMI signals before they can enter the device housing via the terminal pins 16. The filter capacitor 14 comprises a ceramic or ceramic-based dielectric monolith 36 having multiple capacitor-forming conductive electrode plates formed therein. The capacitor dielectric 36 preferably has a circular cross-section matching the cross-section of the ferrule 18 and supports a plurality of spaced-apart layers of first or "active" electrode plates 38 in spaced relationship with a plurality of spaced apart layers of second or "ground" electrode plates 40. The filter capacitor 14 is preferably joined to the feedthrough 12 adjacent to the insulator side 26 by an annular bead 42 of conductive material, such as a solder or braze ring, or a thermal-setting conductive adhesive, and the like. The dielectric 36 includes lead bores 44 provided with an inner surface metallization layer. The terminal pins 16 pass there through and are conductively coupled to the active plates 38 by a conductive braze material 46 contacting between the terminal pins 16 and the bore metallization. In a similar manner, the ground plates 40 are electrically connected through an outer surface metallization 48 and the conductive material 42 to the ferrule 18.

It is appreciated that various modifications to the invention concepts described herein may be apparent to those of ordinary skill in the art without departing from the scope of the present invention as defined by the appended claims.

What is claimed is:

1. A feedthrough assembly, which comprises:
   a) an insulator of electrically non-conductive material comprising an outer insulator sidewall extending from a first insulator end to a second insulator end, the insulator having at least one terminal pin bore extending through the insulator to the first and second insulator ends;
   b) a metallization comprising a first metal layer contacting at least one of the outer insulator sidewall and the terminal pin bore with a second metal oxide layer adhered to at least a portion of the first metal layer, wherein the first metal is selected from the group consisting of titanium, niobium, molybdenum, tungsten, aluminum, vanadium, and alloys thereof, and the second metal oxide layer is an oxide of the first metal, and wherein the metallization comprising the first metal layer and the second metal oxide layer has a thickness ranging from about 0.01 micrometers (μm) to about 25 micrometers (μm);

c) a terminal pin received in the terminal pin bore, the terminal pin having a sidewall extending to opposed first and second terminal pin ends disposed spaced from the respective first and second insulator ends;

d) a ferrule of an electrically conductive material comprising a ferrule opening defined by a surrounding inner ferrule sidewall, wherein the insulator is supported in the ferrule opening;

e) a first braze material extending from the second metal oxide layer of the metallization contacting the terminal pin bore in the insulator or, from the first metal layer contacting the terminal pin bore, as the case may be, to the terminal pin sidewall to thereby hermetically seal the terminal pin to the insulator; and f) a second braze material extending from the second metal oxide layer of the metallization contacting the outer insulator sidewall or, from the first metal layer contacting the outer insulator sidewall, as the case may be, to the inner ferrule sidewall to thereby hermetically seal the insulator to the ferrule, g) wherein at least one of the first and second braze materials contact the second metal oxide layer.

2. The feedthrough assembly of claim 1 wherein the second metal oxide is characterized as a result of the first metal layer having been subjected to a heat treatment of from about 200° C. to about 1,000° C. for about 30 minutes to about 180 minutes.

3. The feedthrough assembly of claim 1 wherein the second metal oxide layer is selected from the group consisting of titanium oxide, molybdenum oxide, tungsten oxide, aluminum oxide, vanadium oxide, and alloys thereof.

4. The feedthrough assembly of claim 1 wherein the second metal oxide layer has a thickness that ranges from about 0.0025 micrometers (μm) to about 12.5 micrometers (μm).

5. The feedthrough assembly of claim 1 wherein the metallization is adhered to a portion of the terminal pin bore.

6. The feedthrough assembly of claim 1 wherein the metallization is adhered to a portion of the insulator sidewall.

7. The feedthrough assembly of claim 1 wherein a third metal layer is adhered to an outer surface of the second metal oxide layer.

8. The feedthrough assembly of claim 7 wherein a fourth metal oxide layer is contacted to the third metal layer, the fourth metal oxide layer having a thickness ranging from about 0.01 micrometers (μm) to about 2.0 micrometers (μm).

9. The feedthrough assembly of claim 1 wherein the first metal layer is applied to one of the outer insulator sidewall and the terminal pin bore in the insulator by a means selected from the group consisting of sputtering, electron-beam deposition, pulsed laser deposition, plating, electroless plating, chemical vapor deposition, vacuum evaporation, thick film application methods, and aerosol spray deposition, and thin cladding.

10. The feedthrough assembly of claim 1 wherein the terminal pin is composed of a material selected from the group consisting of platinum, platinum alloys, gold, silver, palladium, palladium alloys, niobium, and tantalum.

11. The feedthrough assembly of claim 1 wherein the insulator is composed of a material selected from the group consisting of alumina, zirconia, zirconia toughened alumina, aluminum nitride, boron nitride, silicon carbide, glass, and combinations thereof.

12. The feedthrough assembly of claim 1 wherein the electrically conductive material of the ferrule is selected from the group consisting of titanium, tantalum, niobium, stainless steel, and combinations of alloys thereof.

13. The feedthrough assembly of claim 1 wherein the first and second braze materials are selected from the group consisting of gold, gold alloys, and silver.

14. The feedthrough assembly of claim 1 wherein the first metal is titanium and the second metal oxide is selected from $Ti_2O_3$ and $TiO_2$.

15. A feedthrough assembly, which comprises:
a) an insulator of electrically non-conductive material comprising an outer insulator sidewall extending from a first insulator end to a second insulator end, the insulator having at least one terminal pin bore extending through the insulator to the first and second insulator ends;

b) a metallization comprising titanium as a first metal layer contacting at least one of the outer insulator sidewall and the terminal pin bore with a second metal oxide comprising at least one of $Ti_2O_3$ and $TiO_2$ as a result of the first metal layer having been subjected to a heat treatment of from about 200° C. to about 1,000° C. for about 30 minutes to about 180 minutes adhered to at least a portion of the first metal layer, wherein the metallization comprising the first metal layer and the second metal oxide layer has a thickness ranging from about 0.01 micrometers (μm) to about 25 micrometers (μm);

c) a terminal pin received in the terminal pin bore, the terminal pin having a sidewall extending to opposed first and second terminal pin ends spaced from the respective first and second insulator ends;

d) a ferrule of an electrically conductive material comprising a ferrule opening defined by a surrounding inner ferrule sidewall, wherein the insulator is supported in the ferrule opening;

e) a first braze material extending from the second metal oxide layer of the metallization contacting the terminal pin bore in the insulator or, from the first metal layer contacting the terminal pin bore, as the case may be, to the terminal pin sidewall to thereby hermetically seal the terminal pin to the insulator; and f) a second braze material extending from the second metal oxide layer of the metallization contacting the outer insulator sidewall or, from the first metal layer contacting the outer insulator sidewall, as the case may be, to the inner ferrule sidewall to thereby hermetically seal the insulator to the ferrule, g) wherein at least one of the first and second braze materials contact the second metal oxide layer.

16. A feedthrough assembly, which comprises:
a) an insulator of electrically non-conductive material comprising an outer insulator sidewall extending from a first insulator end to a second insulator end, the insulator having at least one terminal pin bore extending through the insulator to the first and second insulator ends;

b) a metallization comprising titanium as a first metal layer contacting the outer insulator sidewall and the terminal pin bore with a second metal oxide layer comprising at least one of $Ti_2O_3$ and $TiO_2$ adhered to at least a portion of the first metal layer, wherein the metallization comprising the first metal layer and the second metal oxide layer has a thickness ranging from about 0.01 micrometers (μm) to about 25 micrometers (μm);

c) a terminal pin received in the terminal pin bore, the terminal pin having a sidewall extending to opposed first and second terminal pin ends disposed spaced from the respective first and second insulator ends;

d) a ferrule of an electrically conductive material comprising a ferrule opening defined by a surrounding inner ferrule sidewall, wherein the insulator is supported in the ferrule opening;

e) a first braze material, extending from the second metal oxide layer of the metallization contacting the terminal pin bore in the insulator to the terminal pin sidewall to thereby hermetically seal the terminal pin to the insulator; and f) a second braze material extending from the second metal oxide layer of the metallization contacting the outer insulator sidewall to the inner ferrule sidewall to thereby hermetically seal the insulator to the ferrule.

* * * * *